United States Patent [19]

Vold

[11] Patent Number: 4,929,544

[45] Date of Patent: *  May 29, 1990

[54] REAGENTS, METHODS, AND TEST KIT FOR DIAGNOSING/MONITORING CANCER IN HUMANS

[75] Inventor: Barbara S. Vold, Menlo Park, Calif.

[73] Assignee: SRI International, Menlo Park, Calif.

[*] Notice: The portion of the term of this patent subsequent to May 21, 2004 has been disclaimed.

[21] Appl. No.: 900,634

[22] Filed: Aug. 27, 1986

Related U.S. Application Data

[63] Continuation-in-part of Ser. No. 532,998, Sep. 16, 1983, Pat. No. 4,665,018, which is a continuation-in-part of Ser. No. 371,287, Apr. 23, 1982, abandoned.

[51] Int. Cl.$^5$ .................. G01N 33/577; G01N 33/574
[52] U.S. Cl. ........................................... 435/6; 435/7; 435/702.1; 435/172.2; 435/810; 435/240.27; 436/536; 436/537; 436/542; 436/548; 436/64; 436/94; 436/804; 436/808; 436/809; 436/813; 436/815; 436/822; 935/104; 935/110; 530/387
[58] Field of Search ................ 424/1.1, 85, 88; 435/4, 435/6, 7, 68, 172.2, 240.27, 810, 948; 436/501, 504, 518, 528–534, 536–538, 542, 548, 63, 64, 94, 804, 808–810, 813, 815, 822, 823; 530/387, 388; 935/100, 104, 108, 110

[56] References Cited

U.S. PATENT DOCUMENTS 4,665,018  5/1987  Vold ........................................ 435/6

OTHER PUBLICATIONS

Vold, B. S. et al., "Use of a Monoclonal Antibody to Detect Elevated Levels of a Modified Nucleoside, N-[-9-(B-D-Ribo-furanosyl)purin-6-ylcarbamoyl]-L--threonine, in the Urine of Breast Cancer Patients," Canc. Res. 46:3164–3167, Jun. 1986.

Primary Examiner—Margaret Moskowitz
Assistant Examiner—Kay E. Cheney
Attorney, Agent, or Firm—Irell & Manella

[57] ABSTRACT

Human cancer is diagnosed/monitored by measuring the levels of N-[9-($\beta$-D-ribofuranosyl)purin-6-ylcarbamoyl]-L-threonine (t$^6$A), in a physiological fluid specimen of a subject by a quantitative immunoassay that employs a monoclonal anti-t$^6$A antibody and comparing that level to the level of t$^6$A that occurs in corresponding physiological fluid of normal subjects to determine whether the former is substantially elevated over the latter or by comparing that level to the level of t$^6$A present in specimens taken from the subject at different times.

20 Claims, 3 Drawing Sheets

REAGENTS, METHODS, AND TEST KIT FOR DIAGNOSING/MONITORING CANCER IN HUMANS

REFERENCE TO GOVERNMENT GRANT

The invention described herein was, in part, made in the course of work under a grant from the National Institute of Health, Department of Health and Human Services, and the National Science Foundation.

CROSS-REFERENCE TO RELATED APPLICATIONS

This application is a continuation-in-part of copending U.S. application Ser. No. 532,998, filed Sept. 16, 1983 now U.S. Pat. No. 4,665,018 issued May 12, 1987, which in turn is a continuation-in-part of copending U.S. application Ser. No. 371,287, filed April 23, 1982 and now abandoned.

DESCRIPTION

1. Technical Field

The invention is in the field of cancer diagnosis and monitoring. More particularly it concerns a method for diagnosing cancer or monitoring the status of cancer in patients already diagnosed as having cancer by determining the amount of N-[9($\beta$-D-ribofuranosyl) purin-6-ylcarbamoyl]-L-threonine ($t^6A$) in urine by immunoassay.

2. Background Art

Ribonucleic acids (RNAs), particularly transfer RNAs (tRNAs). contain a variety of modified nucleosides which are formed after transcription of the macromolecule. Nishimura, S., *Transfer RNA: Structure, Properties and Recognition*, Schimmel, P. R.. et al, eds, Cold Springs Harbor Laboratory (1979), reports that over 50 of these modified nucleosides have been isolated and characterized. When these RNAs are degraded, the majority of modified nucleosides do not appear to be catabolized to any extent in animals or humans and are excreted in significant amounts in urine. Since tRNAs are the most highly modified class of RNAs, it has been assumed that turnover of tRNA is the source of excreted modified nucleosides. Evidence for a higher turnover rate for tRNA in tumor tissue and evidence for intracellular scavenging of tRNAs with structural abnormality have been reported. Borek, E., et al, *Cancer Res* (1977) 37:3362–3366 and Nomura, Y., *FEBS Lett* (1974) 45:223–227.

Prior to applicant's invention only six of the fifty plus known naturally occurring modified nucleosides had been reported to be elevated in cancer patients. The six include four methylated nucleosides (1-methylinosine, $N^2$, $N^2$-dimethyladenosine, 2-methylguanosine, and 1-methyladenosine), 20 pseudouridine, and $N^4$-acetylcytidine. Gehrke, C. W., et al. *Cancer Res* (1979) 39:1150–1153, Speer, J., et al, *Cancer* (1979) 44:2120–2123, and Borek, E., *Cancer Markers* (1980) Sell, S. (ed.). Humana Press report measuring elevated amounts of five of these nucleosides in urine of cancer patients by high performance liquid chromatography (HPLC). The nucleosides are concentrated from the urine, such as by affinity chromatography before being measured. The serum levels of the $\epsilon$-aminocaproate derivatives of $N^2$,$N^2$-dimethylguanosine and pseudouridine in cancer patients determined by radioimmunoassay have also been reported. Levine, et al. *J Natl Cancer Inst* (1975) 54:341–343.

Radioimmunoassays for various modified nucleosides, including $t^6A$, have been used to evaluate the levels of such nucleosides in bacterial tRNAs. Milstone, et al, *Nucl Acids Res* (1978) 5:3439–3455; Vold, B., *Nucl Acids Res* (1979) 7:193–204; and Vold, B. et al, *Nucl Acids Res* (1979) 7:971–980.

A principal object of the present invention is to provide a reproducible, noninvasive method for detecting the presence or status of human cancer based on the levels of $t^6A$ in physiological fluids such as serum or urine. This invention method normally uses unfractionated urine as the test physiological fluid. A monoclonal antibody-based immunoassay is used to determine the amount of $t^6A$ in the fluid. Other objects are to provide novel monoclonal anti-$t^6A$ antibodies and kits containing same for use in such diagnosis or monitoring.

DISCLOSURE OF THE INVENTION

One aspect of the invention is a method for detecting cancer in a human patient comprising:
  (a) determining the amount of N-[9-($\beta$-D-ribofuranosyl)purin-6-ylcarbamoyl]-L-threonine ($t^6A$) in a specimen of a physiological fluid of said patient
    (i) by a quantitative immunoass a specimen is incubated with a monoclonal antibody against $t^6A$ and labeled $t^6A$, or
    (ii) by a competitive inhibition enzyme-linked immunosorbent assay in which a $t^6A$ protein carrier conjugate bound to a solid phase is incubated with the specimen and a monoclonal antibody against $t^6A$ followed by incubation with an enzyme-labeled antibody against the monoclonal antibody: and
  (b) comparing said amount with the standard amount of $t^6A$ present in corresponding physiological fluid of normal human subjects to determine whether said amount is substantially greater than the standard amount.

When this aspect of the invention is used to monitor the status of cancer in a cancer patient the respective amounts of $t^6A$ in physiological fluid specimens taken from the patient at periodic time intervals will be compared.

Another aspect of the invention is a monoclonal antibody against $t^6A$. Hybridomas that produce such antibodies are yet another aspect of the invention.

Kits for use in detecting $t^6A$ in specimens of physiological (body) fluid are also part of the invention. Examples of the kits are:

An enzyme immunoassay kit for determining the amount of $t^6A$ in a physiological fluid of a human comprising in packaged combination a multicontainer unit having:
  (a) a first container containing $t^6A$ conjugated to a carrier protein;
  (b) a second container containing a monoclonal antibody against $t^6A$; and
  (c) a third container containing an enzyme-labeled antibody against said monoclonal antibody, and 2. A radioimmunoassay kit for determining the amount of $t^6A$ in a physiological fluid of a human comprising in packaged combination a multicontainer unit having:
  (a) a first container containing radiolabeled $t^6A$; and (b) a second container containing a monoclonal antibody against $t^6A$.

MODES FOR CARRYING OUT THE INVENTION

Figure 1:
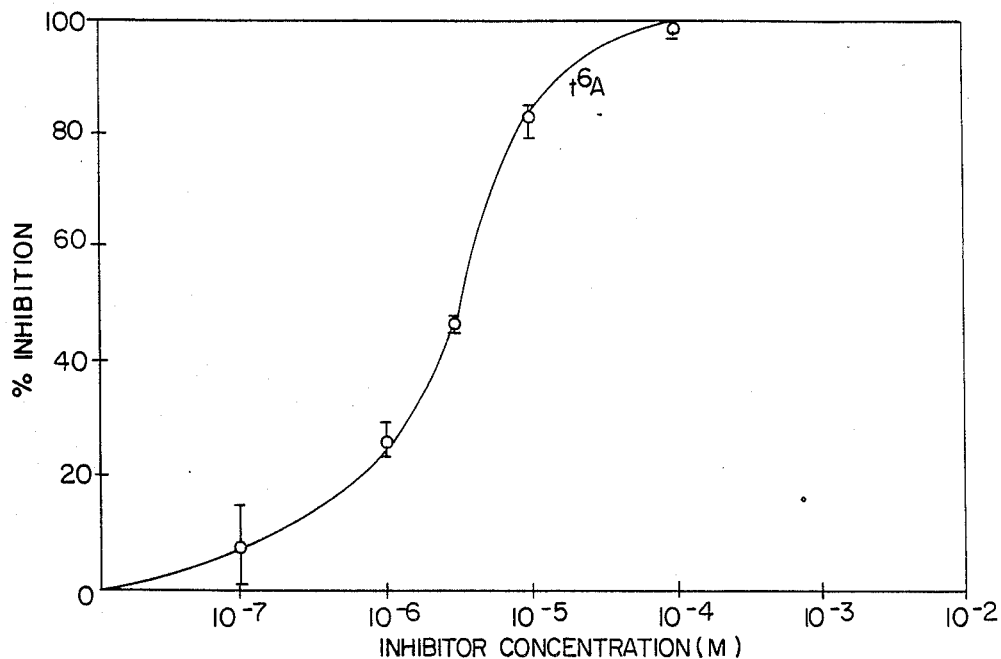
FIG. 1 is a graph showing the results of the radioimmunoassay tests described in Example 2, infra.

The invention methods may be used to diagnose or monitor the status of any type of cellular neoplasm, including carcinomas, myelomas, and lymphomas. These methods are thus useful in diagnosis as in screening programs for early detection of the disease, in therapy as in evaluating the status of the disease after surgical, radiation and/or chemotherapeutic treatment and in prognosis such as in detecting the possibility of recurrence or metastases. Examples of cancers that have been determined to be associated with elevated levels of modified nucleosides are leukemia, lung cancer, Burkitt's lymphoma, melanoma, ovarian cancer, metastatic breast cancer, Hodgkin's disease, colon cancer, and bladder cancer.

The urine samples that are used in the invention methods may be collected randomly or over a given time period, conventionally 24 hours. It has been reported that no significant variation in the levels of modified nucleoside occurs relative to the sample collection regimen (Fischbein, A. et al *Cancer Res* (1983) 43:2971-2974). One of the significant advantages of the invention immunoassay relative to the prior art HPLC method for detecting other modified nucleosides is that the $t^6A$ does not have to be separated from the urine sample prior to being assayed. In the HPLC technique the nucleosides are separated by affinity chromatography from the sample before being assayed. The $t^6A$ also does not have to be derivatized as in the prior art assay. The amount of urine used in the invention methods will usually range between about 1 to about 100 $\mu l$ depending upon the particular antibody involved.

When the assay is used to monitor the status of cancer in a patient already diagnosed to have cancer, the patient's own levels of $t^6A$ in his/her biological fluid serve as an internal control. Decreases signify a reduction in tumor burden such as might occur after the patient has been treated. Increases signify an increase in tumor burden indicating a recurrence or metastases of the cancer. Specimens are taken at predetermined intervals, generally periodically, for convenience, as specified by the physician.

The amount of $t^6A$ in the specimen(s) is determined by a quantitative immunoassay. Various types of quantitative immunoassays such as competitive immunoassays, direct immunoassays and indirect immunoassays may be used. The three most common quantitative immunoassays are radioimmunoassay, quantitative immunofluorescence (both solution and solid phase), and quantitative enzyme assays. Any of these may be used to practice the invention. These assays involve the formation of immune complexes that include a label and the detection of such complexes via the label. As used herein, the term "label" is intended to include moieties that may be detected directly such as fluorochromes and radiolabels as well as moieties such as enzymes that must be reacted or derivatized to be detected. In competitive assays. The sample is incubated with the monoclonal antibody against $t^6A$ and a known amount of labeled $t^6A$. Any $t^6A$ (unlabeled) in the sample competes with the labeled $t^6A$ for antibody. The resulting immune complexes are separated and the amount of labeled complex therein is determined. The amount of modified nucleoside is determined by comparison with the effect of standards. Direct immunoassays involve incubating the sample with a labeled monoclonal antibody against $t^6A$ and separating any immune complexes that form. The amount of label therein is determined and the amount of $t^6A$ in the sample is determined by comparison with the effect of standards. In an indirect immunoassay, such as an enzyme linked immunosorbent assay (ELISA), the antigen bound to a carrier protein such as an albumin is bound (immobilized) to a solid phase (e.g., a tube, bead or well surface). the specimen to be tested is introduced with the monoclonal antibody to $t^6A$, and a second enzyme-labeled antibody against the anti-$t^6A$ monoclonal antibody is added. Immobilized immune complexes are detected via reaction of the enzyme with an appropriate substrate, and the amount of $t^6A$ in the sample is determined by comparison with the effect of standards.

The particular label that is used will depend on the type of quantitative immunoassay used. The assay should be such as to provide sensitivities down to at least about 1 to 10 pmol of modified nucleoside. Examples of labels that may be used are radiolabels such as $^{32}P$, $^{125}I$, $^{3}H$, and $^{14}C$, fluorescent labels such as fluorescein and its derivatives, rhodamine and its derivatives, dansyl, and umbelliferone, chemiluminescers such as luciferia and 2,3-dihydrophthalazinediones, and enzymes, such as horseradish peroxidase, alkaline phosphatase, and glucose-6-phosphate dehydrogenase, or such enzymes used with a biotin/avidin or other amplification system. The antibody or nucleoside, as the case may be, may be tagged with such labels by known methods. For instance, coupling agents such as aldehydes, carbodiimides, dimaleimide, imidates, succinimides, bis-diazotized benzadine, and the like may be used to tag the antibodies with fluorescent, chemiluminescent, or enzyme labels.

The antibodies against $t^6A$ that are used in these immunoassays may be polyclonal (heterologous) or monoclonal (homologous). Polyclonal antibodies may be made by immunizing host animals such as mice, rabbits, and sheep using a $t^6A$ protein carrier conjugate as an immunogen. The immunization will typically involve repeated inoculations with the immunogen. Such inoculation will raise an immune response against the immunogen and cause the inoculated host's immune system to produce antibodies against $t^6A$. Serum from the immunized host will usually be collected about three to ten days after the final booster. Immunoglobulins may be separated from the serum by ammonium sulfate precipitation, gel electrophoresis, dialysis, affinity or other chromatography, or other conventional separation and purification techniques, if desired.

Monoclonal antibodies against the $t^6A$ may be made by the somatic cell hybridization techniques of Kohler and Milstein, *Nature* (1975) 265:495 using antibody-producing cells, e.g. spleen or lymphoid cells, from the immunized host animal. Preferably a mouse, as one of the hybridization partners. The antibody-producing cells are hybridized (fused) with an appropriate cancer (myeloma) cell line using a fusogen such as polyethylene glycol having a Mw of 1,000 to 14,000 daltons. A myeloma cell line that is sensitive to a selective medium such as HAT medium (Littlefield, *Science* (1969) 145:709–710), fuses efficiently, and will support stable high level expression and secretion of antibody by its hybridization partner is used. While myeloma cells from any species such as those indicated above with respect to polyclonal antibodies may be used, murine and rat myeloma lines having these characteristics are available currently and are preferred. Examples of such lines are those derived from the original MOPC-21 and MPC-11 mouse tumors that are available from the Salk Institute Cell Distribution Center, P.O. Box 1809, San Diego, Calif. 92112. A myeloma cell:antibody-producing cell ratio in the range of about 1:lo and about 10:1 will normally be used. The individual cell concentrations will typically be in the range of about $10^6$ to $10^8$, preferably $1 \times 10^7$, cells/ml fusion medium. Balanced salt solutions containing 30% to 60% (w/v). preferably 35% to 50% (w/v) fusogen may be used as a fusion medium. After the fusion. The cells are washed with fusogen-free medium to remove fusogen. They are then seeded and cultivated in the selective medium to eliminate unhybridized parent cells and leave only hybrids that are resistant to the selective medium and possess the immortality of the myeloma parent. The cultivation will normally take about three to five weeks.

Surviving hybridomas may be examined for Production of antibody against $t^6A$ by immunoassay. Positive hybridoma clones may be subcloned by limiting dilution techniques and grown in vitro or in vivo by known techniques. The monoclonal anti-$t^6A$ antibody secreted by the subclones may be separated from the culture medium or ascites fluid when grown in vivo by known techniques such as ammonium sulfate precipitation, DEAE cellulose chromatography, or affinity chromatography. Further purification of the antibodies, if desired, may be achieved by ultracentrifugation and microfiltration.

Antibodies against the isotype of the anti-$t^6A$ antibody may be used as the labeled second antibody in indirect assays such as the ELISA. For instance if the anti-$t^6A$ antibody is a murine IgG, anti-murine IgG serum from another mammalian species may be used. Such anti-isotype antibodies may be raised by conventional immunization techniques.

The incubations of the immunoassays will be carried out under conditions that permit reaction between the antibody and modified nucleoside. Temperature, pH and duration are the most important process conditions in the incubation. Temperatures in the range of about 5° C. to 40° C., preferably about 37° C., will typically be used. The pH will normally be about 6 to 9, preferably about 7. and the binding reaction will usually reach equilibrium in about 10 minutes to 2 days, depending upon the particular antibodies involved. Antibody will be used in limiting amounts in the competitive assays. Immune complexes may be separated from the incubation mixture by centrifugation or other conventional techniques. Separation may not be necessary in assays such as the homogenous enzyme immunoassay (EMIT). Conventional buffer media may be used for any washing steps involved in the assays.

The label detection means used in the immunoassay will depend upon the particular label involved. For instance, radiolabels may be detected with scintillation counters, fluorescent labels with fluorescent microscopes (fluorometers) and enzyme labels with colorimeters that detect the magnitude of color change caused by the reaction between the enzyme and the substrate or spectrophotometers (e.g. microtiter plate readers).

The basic ingredients of the test kit for carrying out the $t^6A$ radioimmunoassay of the invention are labeled $t^6A$ and monoclonal antibody against $t^6A$. These ingredients will typically be in solution in an appropriate aqueous solvent and contained in suitable dispensers. Solid phase kits will contain a solid phase (tube, microtiter plate, or bead) and, optionally, a coupling agent such as an aldehyde or carbodiimide to bind the antibody to the solid phase. ELISA kits will contain $t^6A$ carrier protein conjugate, anti-$t^6A$ monoclonal antibody, enzyme-labeled antibody against the monoclonal antibody and a suitable substrate. The kits may also contain a suitable buffer for dilution and washes, carrier protein, unlabeled $t^6A$ for preparing standards, a postcoating preparation to reduce nonspecific bonding to solid phase, containers in which the reagents may be used, and directions for performing the assay. The components of the kit may be packaged in a conventional manner.

As indicated above and as illustrated by the examples, infra, in which rabbit anti-$t^6A$ serum and murine monoclonal anti-$t^6A$ antibodies are used in the invention, the species of the antibody is not critical. Likewise, as evidenced by the use of rabbit antisera in the invention method (Example 1, infra) the class (subclass) of antibody does not appear to be critical. In this regard although only a limited number of $t^6A$ monoclonal antibodies are described in the examples, it is intended that the invention encompass all anti-$t^6A$ monoclonal antibodies, regardless of species or class, that are functionally equivalent to the described monoclonal antibody. Functionally equivalent monoclonal antibodies are those that bind specifically to $t^6A$. In this regard, the subclasses of IgG differ from one another in their constant region. However, an IgG against a specific antigen will have a functionally equivalent variable region regardless of its subclass. Accordingly, although the exemplified monoclonal antibody is an IgG of a particular subclass, functional monoclonal antibodies of other IgG subclasses or other classes (IgM, IgA, etc.) are intended to be within the scope of the invention.

The following examples further illustrate the invention methods. These examples are not intended to limit the invention in any manner.

EXAMPLE 1

Urine Samples. 24 hour urine samples were obtained from patients with various advanced malignancies, previously untreated with chemotherapy, and normal volunteers at the Cancer Center of the University of New Mexico. The urines were collected from each individual inn plastic containers for 24 hours and kept under refrigeration until the end of collection. The urine volume was then measured and an aliquot of urine was kept frozen until the day of analysis. The amount of creatinine for each sample was determined by the colorimetric method described in the Sigma Technical Bulletin No. 555:1–12, 1977.

Antibody preparation. Immunogen was prepared by conjugating $t^6A$ to bovine serum albumin (BSA) using the method of Erlanger and Beiser, PNAS (1964) 52:68–74. Antibodies were made in rabbits; a total of 5 mg immunogen (mixed with complete Freund's adjuvant) per rabbit was introduced in three injections into the hind legs on days 0, 14, and 21. The immunized rabbits were bled on day 28. Serum was precipitated twice at 0° C. with 50% saturated ammonium sulfate (SAS), pH 7.0, and then dialyzed against 0.14 M NaCl. 10 mM sodium phosphate, pH 7.0 (PBS)

Tritiated Antigen. Tritiated $t^6A$ was prepared by catalytic (Pt) exchange with tritiated water. $[^3H]t^6A$, 0.84 Ci/mmol, was 88% pure by 2D thin layer chromatography analysis using the solvent system described by Rogg, et al, *Nucleic Acids Res* (1976) 3:285-295, and 6.9 Pmol was used per assay.

Radioimmunoassay. The saturated ammonium sulfate radioimmunoassay (SAS-RIA) for $t^6A$ described by Vold, B. S., *Nucleic Acids Res* (1979) 7:193-204 was used. Assays were done in 12×75 mm polypropylene tubes in a total reaction volume of 300 μl with 75 mM NaCl, 0.1 M boric acid, 25 mM sodium tetraborate, pH 8.3. Normal rabbit IgG was used to adjust the total protein concentration of each assay to 600 μg. The buffer, antibody, carrier protein, $[^3H]t^6A$, and untreated urine were mixed well, incubated at 37° C. for 1 hour, then cooled on ice for 5 min. The amount of urine used was chosen such that normal urine would give inhibition values between 10% and 40%. Thus, 2 μl of urine was used in each assay. An equal volume of ice-cold SAS was added to each tube, mixed thoroughly, and incubated at 0° C. for 30 minutes. The tubes were then centrifuged at 9,400 x g for 15 minutes at 4° C., and the supernatant removed by aspiration through a capillary pipette. The pellets were resuspended in 200 μl of 50% SAS in borate saline buffer, mixed centrifuged, and drained as before. The washed pellets were then suspended in 200 μl of 1X borate saline buffer, mixed, and a 75 μl added to 5 ml of Aquasol scintillation fluid. Radioactivity was then measured in a scintillation counter. Under the conditions used for competitive inhibition, cPm bound on the filter without inhibitor and with (or without) antiserum was 1133 (66) for $t^6A$. When urine was added as a source of competitive inhibitor and the same assay repeated on four different occasions, standard deviation was ±3.7%.

The concentration of inhibitor present in each urine sample was interpolated from a graph of % trace binding for the antibody when the cognate modified nucleoside had been used as competitive inhibitor. These concentrations were then normalized to the creatinine level in each sample expressed as nmol nucleoside/μmol creatinine. Speer, et al, *Cancer* (1979) 44:20-2123.

Urine samples from 8 normal patients, 4 Hodgkin's patients, 4 non-Hodgkin's lymphoma patients, 5 lung cancer patients (small cell, adenocarcinoma, squamous cell, and large cell) and 8 "other" cancer patients (breast, head and neck, bowel) were tested. None of the patients had been treated previously by chemotherapy. Assay results for the cancer patients were compared by group with the assay results from the normal patients. Significance of variation in the levels of $t^6A$ in the samples was established using a t test comparing each cancer group to the normal group. A P value less than 0.05 was considered a significant variation (using 95% confidence levels). The results of these comparison were:

SIGNIFICANCE OF VARIATION (P)

| Significance of Variation (P) | | | |
|---|---|---|---|
| Lymphomas | | Solid Tumors | |
| Hodgkin's | Non-Hodgkins | Lung | Other |
| not significant | P < 0.05 | P < 0.001 | P < 0.02 |

As these data indicate, elevated levels of $t^6A$ in urine is a clear marker for all the cancers tested except perhaps Hodgkin's disease. The lack of significant variation in the Hodgkin's patients may be attributable to the small number of patients involved.

EXAMPLE 2

Monoclonal Antibody Preparation. A BALB/c mouse was immunized with the $t^6A$-BSA conjugate of Example 1 (100 μg) in complete Freund's adjuvant intraperitoneally at day 0. At day 7 the mouse was boosted with 100 μg of the conjugate in PBS intravenously. The mouse spleen was removed at day 10. Spleen cells were fused with P3/63/Ag 8.653 murine myeloma cells according to Kennet's fusion protocol (Kennet. et al, (1979) "Cell Fusion", in *Methods in Enzymology*, Academic Press, N.Y. pp.345-357). The fusogen was polyethylene glycol (1540 mW) at 38% W/v.

Media from wells containing surviving cells were tested for anti-$t^6A$ antibody by radioimmunoassay. Cells from one of the positive wells (#G8) were subcloned by limiting dilution into wells containing normal mouse spleen cells as feeders. Subclones were tested for antibody production by radioimmunoassay and one, identified as G8-3, was chosen as a source of monoclonal anti-$t^6A$ antibody.

Cells from clone G8-3 were then frozen, reestablished in culture, and subcloned a second time in vitro according to the same procedure as the first subcloning. Two subclones from the second subcloning were retained (#9D4 and #5C4). Cells from line #9D4 were selected to be the established cell line.

The screening of the clones was done using a solid phase assay. A conjugate of $t^6A$ to human serum albumin was made and used to coat wells of a microtiter plate. Culture fluid was than added followed by a second antibody which was labeled with $^{125}I$ and which recognizes mouse IgG. A sample of line #9D4 was deposited in the American Type Culture Collection 12301 Parklawn Drive, Rockville, Md. 20852, U.S.A. on Aug. 23, 1983. This sample was assigned ATCC number HB8351.

Protein from the culture fluid of #9D4 was isolated by means of an affinity column chromatography step using protein A-Sepharose CL-4B. Isotyping of the resulting immunoglobin indicated it to be $IgG_1,\kappa$. The bound fraction from this column was tested in various quantitative immunoassays for $t^6A$ as described below.

Radioimmunoassay. The SAS-RIA referred to in Example 1 was used. Reaction volume was 300 μl, and the total protein content was normalized using carrier normal rabbit immunoglobulins—typically 200-600 μg to total protein/assay. Reactions containing 80 μg of the above described monoclonal antibody fraction 15 pmol $[^3H]t^6A$, varying concentrations of unlabeled $t^6A$, and carrier protein were incubated for 1 hour at 37° C. in borate-saline buffer: 75mM NaCl. 0 1 M boric acid, 25 mM sodium tetraborate, pH 8.3. After the reactions were cooled on ice, an equal volume of cold SAS was added. The solution was mixed thoroughly, and the incubation was continued for 30 minutes at 0° C. At the end of the 30 minutes incubation, the suspensions were centrifuged for 15 minutes at 4° C. and 9,400 x g and the supernatant fluid was removed by aspiration. The pellet was resuspended in 500 μl of ice-cold 50% SAS in borate-saline buffer, mixed, recentrifuged, and drained as before. The washed pellets were then resuspended in 500 μl of borate-saline buffer and transferred to 5 ml of Aquasol scintillation fluid. Radioactivity was measured in a scintillation spectrophotometer. The results are shown in FIG. 1.

ELISAs. Two ELISA techniques were tested: one using alkaline phosphatase, the other horseradish peroxidase (HRP). In each technique, microtiter plates were washed once with tap water and once with distilled water. Then each well was filled with 50 μl of 10 μg/ml $t^6A$ conjugated to human serum albumin ($t^6A$-HSA) in 1 M NaCl and 0.02 M sodium phosphate (pU 7.0), and left overnight at 4° C. Each well was emptied and washed (3×100 μl) with 1% HSA in PBS. Wells were then filled with a solution without antibody or various dilutions of hybridoma culture fluid in PBS. after incubation at room temperature for 2 to 3 hours, wells were emptied and washed (3×100 μl) with 1% HSA in PBS. Then each well was incubated with 50 μl of a dilution of enzyme-anti-mouse IgG conjugate. Each type of reaction was then treated differently, as described below.

Alkaline phosphatase. To each well was added 50 μl of a 1/500 dilution of goat anti-mouse IgG conjugated to alkaline phosphatase. After standing at room temperature for 2 to 3 hours, the wells were emptied, washed (3×100 μl) with 10% diethanolamine (pH 9.8). The enzyme-substrate reaction was incubated 30 minutes at room temperature and stopped with 100 μl of 3N NaOH. Absorbance at 405 nm was read in an Automated Microtiter Plate Reader (Micro ELISA Autoreader MR 580, Dynatech).

Horseradish peroxidase. To each well was added 50 μl of a 1/500 dilution of goat anti-mouse IgG conjugated to horseradish peroxidase. After standing at room temperature for 2 to 3 hours, the wells were emptied and washed once with water and twice with 0.05% Triton X-100 surfactant in PBS. To each well was added 100 μl of the following solution: 0.1 ml of 15 mg 2,2'-azino-Dl-(3-ethylbenzthiazoline sulfonic acid) (ABTS) per ml of $H_2O$, 0.33 ml of 0.3% $H_2O_2$, and 10 ml of citrate buffer (0.105g of citric acid in 10 ml of $H_2O$ adjusted to pH 4.0 using 5 M NaOH). After 30 minutes, absorbance at 405 nm was read in an Automated Microtiter Plate Reader.

Figure 2:
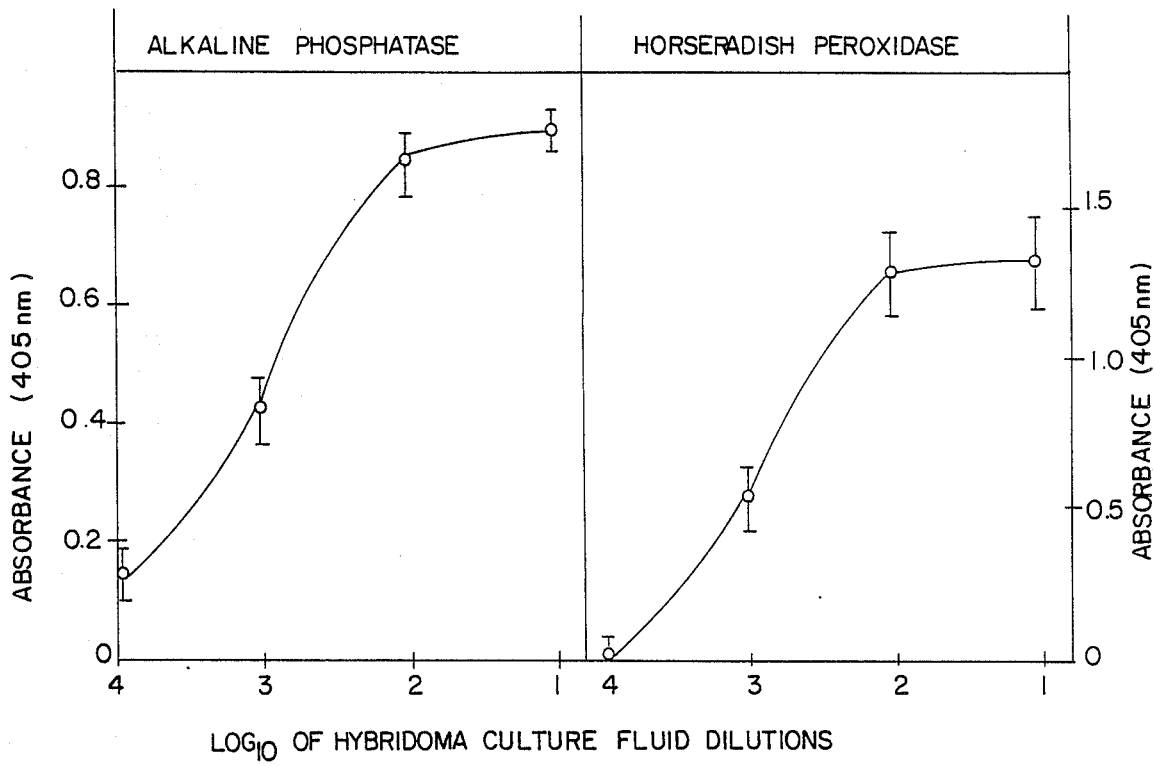
FIG. 2 is a graph showing the results of the two ELISA tests described in Example 2. infra.

FIG. 2 shows the results of these ELISAs.

Figure 3:
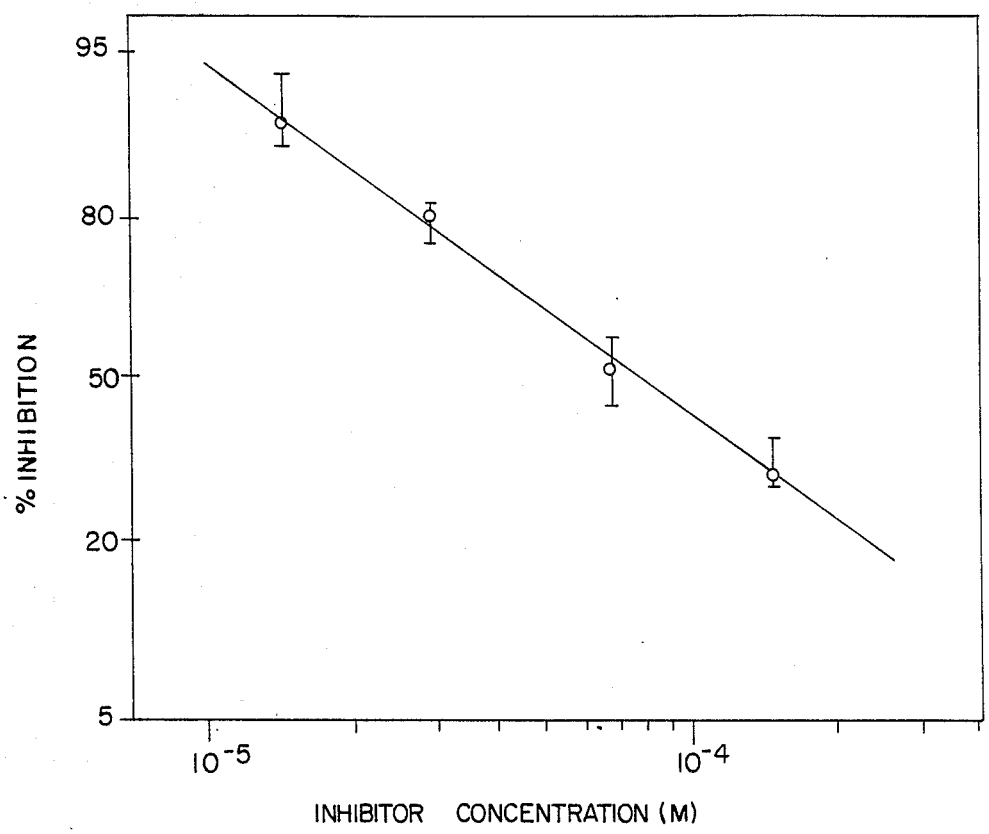
FIG. 3 is a graph showing the results of the competition ELISA test described in Example 2, infra.

A standard curve using a $t^6A$ standard can be prepared for these ELISA techniques using a competitive inhibition procedure in which free $t^6A$ is added to the wells in which the $t^6A$-HSA has been absorbed. A standard curve with the alkaline phosphatase ELISA is shown in FIG. 3. FIG. 3 demonstrates that 50% inhibition of the ELISA Was achieved at a concentration of $t^6A$ of $8.4 \times 10^{-5}$ M. Using the RIA with the monoclonal antibody gave 50% inhibition at $3.2 \times 10^{-6}$ M. The concentration of $t^6A$ in normal human urine is typically $2-20 \times 10^{-6}$ M. Since the concentration of $t^6A$ will vary With the urinary output, values of $t^6A$ are usually expressed as a function of creatinine concentration.

EXAMPLE 3

Two additional hybridoma cell lines designated Al0#16 and 4Bl#11 producing antibodies (isotypes $IgG_1,\kappa$ and $IgG_{2A},\kappa$, respectively) specific to $t^6A$ were made. A sample of line A10 #16 was deposited in the American Type Culture Collection (ATCC), 12301 Parklawn Drive, Rockville, Md. 20852, U.S.A., on June 13, 1989 and assigned ATCC Accession No. HB-10168. A sample of line 4B1 #11, was also deposited in the ATCC on June 13, 1989 and was assigned ATCC Accession No. HB-10167. The details of the procedures used to make these lines and the characterization of the lines is set forth below.

Immunization. A multicarrier immunization scheme was employed. The antigen, $t^6A$, was coupled to two types of carrier proteins BSA (as in Example 2) and keyhole limpet hemocyanin (KLH), as suggested by Stahli et al. (Stahli, C., Taehelin, Th. and Miggiano. V. *Methods in Enzymol* (1983) 92:26–36). Both proteins were linked to $t^6A$ by the method of Erlanger and Beiser. PNAS, supra.

Three BALB/c mice received a primary immunization using 100 μg KLH-$t^6A$ and complete Freund's adjuvant (50 μg subcutaneously and 50 μg intraperitoneally (IP)). The second immunization on day 21 was given IP using 100 μg KLH-$t^6A$ and incomplete Freund's adjuvant. Penultimate immunization on day 192 was given intravenously (IV) using 10 μg KLH-$t^6A$. Final immunization on day 193 was with 100 μg BSA-$t^6A$ given to two animals IV and one animal IP. Animals were sacrificed and spleens used for fusions three days subsequent to the final immunization.

Fusion. Spleen cells were fused to mouse SP2/O-Ag14 myeloma cells according to the protocol of Oi and Herzenberg (*Selected Methods in Cellular Immunology*, B. Mishell and S. Shiigi (eds.), W. H. Freeman and Co., San Francisco. 1980, pp. 351–372).

Selection and Subcloning. Subclones were tested for antibody production by an ELISA utilizing the β-galactosidase/o-nitrophenylgalactopyranoside system (New England Nuclear ELISA kit NEI-606). Positive cultures were subcloned as in Example 2 to obtain monospecific populations of cells.

Figure 4:
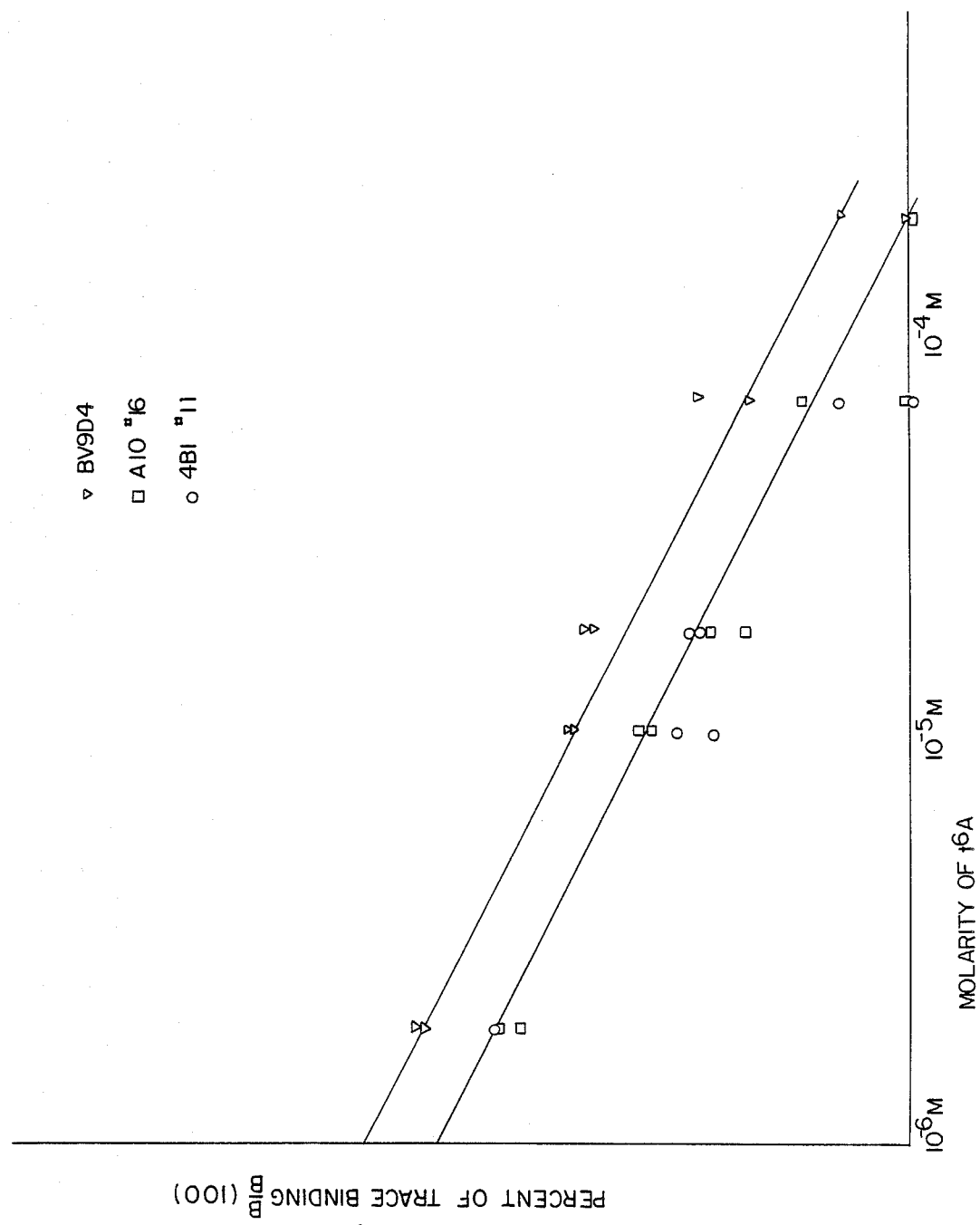
FIG. 4 is a graph of the results of the radioimmunoassay test results described in Example 3, infra.

Characterization of Antibodies. Monoclonal antibodies were precipitated from hybridoma culture fluids using 60% ammonium sulfate. The activity in these preparations were sufficient for testing, so further purification by affinity column chromatography was not employed. For comparison, monoclonal antibody from the cell line #9D4 of Example 2 was made in the same way. All three crude antibody preparations were tested in the radioimmunoassay using [$^3H$]$t^6A$ and ammonium sulfate precipitation as described in Example 2. To linearize the results, the data are plotted in the form of a logit plot (Rodbard, D., Gridson, W., and Rayford, P. L., *J Lab Clin Med* (1969) 74:770–778), and are shown in FIG. 4. Using these antibody preparations, 50% inhibition of #9D4 was achieved at a $t^6A$ concentration of $3.0 \times 10^{-6}$ M, which compares well with the value reported in Example 2 ($3.2 \times 10^{-6}$ M $t^6A$). As shown in FIG. 4, antibodies A10#16 and 4Bl#11 both showed 50% inhibition at $1.3 \times 10^{-6}$ M $t^6A$.

Modifications of the above-described modes for carrying out the invention that are obvious to those of ordinary skill in the the immunodiagnostic art and/or related arts are intended to be within the scope of the following claims.

I claim:

1. A method for detecting cancer in a human patient comprising:
   (a) determining the amount of N-[8 9-(beta-D-ribofuranosyl)purin-6-ylcarbamoyl[9 -L-threonine ($t^6A$) in a specimen of physiological fluid from the patient by a quantitative immiunoassay in which the specimen is incubated with a monoclonal antibody that specifically binds $t^6A$; and
   (b) then comparing said amount with the standard amount of $t^6A$ present in corresponding physiological fluid of normal human subjects to determine whether said amount is substantially greater than the standard amount, a substantially greater amount being an indication of the presence of cancer.

2. The method of claim 1 wherein the monoclonal antibody is a monoclonal antibody produced by hybridoma ATCC HB1068 or ATCC HB10167.

3. The method of claim 1 wherein the immunoassay is a competitive inhibition enzyme-linked immunosorbent assay in which a $t^6A$-protein carrier conjugate bound to a solid phase is incubated with the specimen and the monoclonal antibody followed by incubation with an enzyme-labeled antibody that specifically binds the monoclonal antibody.

4. The method of claim 1 wherein the immunoassay is a competitive assay wherein the specimen is incubated with the monoclonal antibody and labeled $t^6A$.

5. A method for monitoring the status of cancer in a human cancer patient comprising:
   (a) obtaining specimens of physiological fluid from the patient at predetermined time intervals;
   (b) determining the amounts of $t^6A$ in the specimens by a quantitative imminoassay in which the specimens are incubated with a monoclonal antibody that specifically binds $t^6A$; and
   (c) comparing the amounts, with an increase in amount being an indication of increased tumor burden and a decrease in amount being an indication of decreased tumor burden.

6. The method of claim 5 wherein the monoclonal antibody is a monoclonal antibody produced by hybridoma ATCC HB10168 or ATCC HB10167.

7. The method of claim 5 wherein the immunoassay is a competitive inhibition enzyme-linked immunosorbent assay in which a $t^6A$-protein carrier conjugate bound to a solid phase is incubated with the specimens and the monoclonal antibody followed by incubation with an enzyme-labeled antibody that specifically binds the monoclonal antibody.

8. The method of claim 5 wherein the immunoassay is a competitive assay wherein the specimens are incubated with the monoclonal antibody and labeled $t^6A$.

9. A radioimmunoassay kit for determining the amount of $t^6A$ in a physiological fluid of a human comprising in packaged combination a multicontainer unit having:
   (a) a first container containing radiolabeled $t^6A$;
   (b) a second container containing a monoclonal antibody that specifically binds $t^6A$.

10. The kit of claim 9 wherein the monoclonal antibody is a monoclonal antibody produced by hybridoma ATCC HB10168 or ATCC HB10167.

11. An enzyme immunoassay kit for determining the amount of $t^6A$ in a physiological fluid of a human comprising in packaged combination a multicontainer unit having:
    (a) a first container containing $t^6A$ conjugated to a carrier protein;
    (b) a second container containing a monoclonal antibody that specifically binds $t^6A$; and
    (c) a third container containing an enzyme-labeled antibody that specifically binds the monoclonal antibody.

12. The kit of claim 11 wherein the monoclonal antibody is a monoclonal antibody produced by hybridoma ATCC HB10168 or ATCC HB10167.

13. A monoclonal antibody that specifically binds $t^6A$.

14. The monoclonal antibody of claim 13 wherein the monoclonal antibody is produced by hybridoma ATCC HB 8351.

15. The monoclonal antibody of claim 13 wherein the monoclonal antibody is produced by hybridoma ATCC HB10168.

16. The monoclonal antibody of claim 13 wherein the monoclonal antibody is produced by hybridoma ATCC HB10167.

17. A hybridoma that produces a monoclonal antibody that specifically binds $t^6A$.

18. The hybridoma of claim 17 wherein the hybridoma is ATCC HB 8351.

19. The hybridoma of claim 17 wherein the hybridoma is ATCC HB10168.

20. The hybridoma of claim 17 wherein the hybridoma is ATCC HB10167.

* * * * *